United States Patent [19]

Abdulla

[11] 4,319,916

[45] Mar. 16, 1982

[54] 3-ACYL-5-PHENYL-4(1H)-PYRIDINONES AND THEIR USE AS HERBICIDES

[75] Inventor: Riaz F. Abdulla, Greenfield, Ind.

[73] Assignee: Eli Lilly and Company, Indianapolis, Ind.

[21] Appl. No.: 179,598

[22] Filed: Aug. 21, 1980

[51] Int. Cl.$^3$ ............... A01N 43/40; C07D 213/26
[52] U.S. Cl. ........................... 71/94; 71/66; 71/67; 546/298
[58] Field of Search ............ 71/94; 546/298, 315, 546/314

[56] References Cited

U.S. PATENT DOCUMENTS

| | | | |
|---|---|---|---|
| 3,891,661 | 6/1975 | Sugisaka | 546/315 X |
| 3,974,167 | 8/1976 | Hashimoto | 546/315 X |
| 4,065,290 | 12/1977 | Taylor | 71/94 |
| 4,152,136 | 5/1979 | Taylor | 71/90 |

OTHER PUBLICATIONS

Caramella et al. Synthesis (1972), pp. 46–48.
Sanders, J. Org. Chem. vol. 41 (1976), pp. 2658–2659.

*Primary Examiner*—Catherine L. Mills
*Attorney, Agent, or Firm*—Riaz F. Abdulla; Arthur R. Whale

[57] ABSTRACT

A series of novel 1-alkyl-3-acyl-5-substituted-phenyl-4(1H)-pyridinones are herbicides, particularly useful in the culture of cotton.

28 Claims, No Drawings

3-ACYL-5-PHENYL-4(1H)-PYRIDINONES AND THEIR USE AS HERBICIDES

BACKGROUND OF THE INVENTION

1. Field of the Invention

This invention belongs to the field of agricultural chemistry, and provides a class of new herbicides and herbicidal methods and compositions making use of the compounds.

2. State of the Art

The agricultural chemical art has used pyridinones as herbicides in the past. U.S. Pat. No. 4,152,136, of Taylor, shows a group of such compounds. Compounds in the scope of that patent have been the subject of articles in the agricultural chemical journals, for example, Waldrep and Taylor, *J. Agric. Food Chem.* 24, 1250-51 (1976).

SUMMARY OF THE INVENTION

This invention provides a series of novel 3-acylpyridinones of the formula

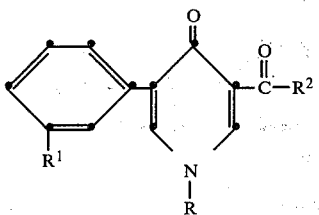

wherein R is $C_1-C_3$ alkyl;

$R^1$ is chloro, bromo, fluoro or trifluoromethyl;

$R^2$ is $C_1-C_4$ alkyl, phenyl, $C_1-C_2$ alkyl substituted with chloro or bromo or monosubstituted with methoxy, or phenyl monosubstituted with chloro, bromo, fluoro or trifluoromethyl.

The compounds are herbicides effective against both terrestrial and aquatic weeds, and algicides. Methods of use of the compounds and compositions containing the compounds are also provided by this invention.

DESCRIPTION OF THE PREFERRED EMBODIMENTS

In this document, all temperatures will be expressed in degrees Celsius. All expressions of concentrations, percentage and the like will refer to weight measurements, unless otherwise stated.

In the above general formula, the general terms $C_1-C_3$ alkyl, $C_1-C_4$ alkyl and $C_1-C_2$ alkyl refer to groups such as methyl, ethyl, isopropyl, propyl, butyl, isobutyl, s-butyl and t-butyl.

Certain classes of the compounds of this invention are preferred. For example, the following limitations describe preferred classes. It will be understood that the limitations set out below as describing individual preferred classes may be combined to constitute further, more limited preferred classes.

(a) R is methyl;
(b) R is methyl or ethyl;
(c) $R^1$ is trifluoromethyl;
(d) $R^1$ is chloro or trifluoromethyl;
(e) $R^2$ is $C_1-C_4$ alkyl;
(f) $R^2$ is $C_1-C_2$ alkyl substituted with chloro.

The preferred individual compounds of this invention are as follows.

1-methyl-3-propionyl-5-(3-trifluoromethylphenyl)-4(1H)-pyridinone
3-acetyl-1-methyl-5-(3-trifluoromethylphenyl)-4(1H)-pyridinone
3-butyryl-1-methyl-5-(3-trifluoromethylphenyl)-4(1H)-pyridinone
1-methyl-3-(2,2-dimethylpropionyl)-5-(3-trifluoromethylphenyl)-4(1H)-pyridinone
1-methyl-3-(2-methylpropionyl)-5-(3-trifluoromethylphenyl)-4(1H)-pyridinone It is believed that the above general formula and description will enable the reader to understand the invention. To assure that it is understood, however, the following exemplary compounds are mentioned.

3-(3-bromophenyl)-5-trichloroacetyl-1-propyl-4(1H)-pyridinone
3-bromoacetyl-5-(3-fluorophenyl)-1-propyl-4(1H)-pyridinone
3-(3-bromophenyl)-5-dibromoacetyl-1-ethyl-4(1H)-pyridinone
3-(2,3,3-tribromopropionyl)-5-(3-fluorophenyl)-1-propyl-4(1H)-pyridinone
3-(3-chlorophenyl)-5-pentachloropropionyl-1-ethyl-4-(1H)-pyridinone
3-(3-bromophenyl)-5-(2,2,3,3-tetrabromopropionyl)-1-methyl-4(1H)-pyridinone
3-(2,3-dichloropropionyl)-3-(3-fluorophenyl)-1-ethyl-4-(1H)-pyridinone
3-tribromoacetyl-1-methyl-5-(3-trifluoromethylphenyl)-4(1H)-pyridinone
3-(4-chlorobenzoyl)-5-(3-chlorophenyl)-1-propyl-4(1H)-pyridinone
3-(3-bromobenzoyl)-5-(3-fluorophenyl)-1-propyl-4(1H)-pyridinone
1-ethyl-3-(2-fluorobenzoyl)-5-(3-trifluoromethylphenyl)-4(1H)-pyridinone
3-(3-bromophenyl)-1-ethyl-5-(4-fluorobenzoyl)-4(1H)-pyridinone
3-(3-fluorophenyl)1-methyl-5-(3-trifluoromethylbenzoyl)-4(1H)-pyridinone
3-(3-chlorophenyl)-1-ethyl-5-(4-trifluoromethylbenzoyl)-4(1H)-pyridinone The compounds of this invention are prepared from a starting compound of the formula

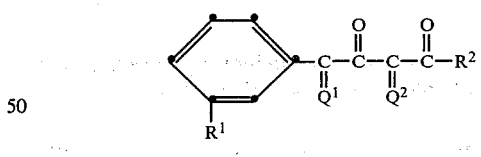

wherein $Q^1$ and $Q^2$ independently represent 2 hydrogen atoms; =CHOH, or an alkali metal salt thereof; =CHN($R^3$)$_2$; or =CHNHR; provided that only one of $Q^1$ and $Q^2$ represents =CHNHR.

The $R^3$ groups independently represent $C_1-C_3$ alkyl, or the $R^3$ groups combine with the nitrogen atom to which they are attached to form pyrrolidino, piperidino, morpholino, N-methylpiperazino and the like.

The =CHOH groups, which may be in the form of alkali metal salts, are provided by reaction with formylating agents which will be defined below. The =CHN($R^3$)$_2$ groups are provided by reaction with aminoformylating agents, and the =CHNHR groups are provided by exchanging either =CHOH groups or =CHN($R^3$)$_2$ groups with amines of the formula $RNH_2$.

When $Q^1$ and $Q^2$ each represent 2 hydrogen atoms, the pyridinones are prepared by either
1. reacting with a formylating or aminoformylating agent;
2. reacting again with a formylating or aminoformylating agent; and
3. reacting with an amine of the formula $RNH_2$; or
1 reacting with a formylating or aminoformylating agent;
2. reacting with an amine of the formula $RNH_2$; and
3. reacting again with a formylating or aminoformylating agent.

When one of $Q^1$ and $Q^2$ represents either $=CHOH$ or $=CHN(R^3)_2$, and the other represents 2 hydrogen atoms, the pyridinones are prepared by either
1. reacting with a formylating or aminoformylating agent; and
2. reacting with an amine of the formula $RNH_2$; or
1. reacting with an amine of the formula $RNH_2$; and
2. reacting with a formylating or aminoformylating agent.

When each of $Q^1$ and $Q^2$ represent either $=CHOH$ or $=CHN(R^3)_2$, the pyridinones are prepared by reacting with an amine of the formula $RNH_2$.

The variations of the synthesis, and the preparation of the intermediates, will be sketched below.

When the process starts with a ketone of the general formula

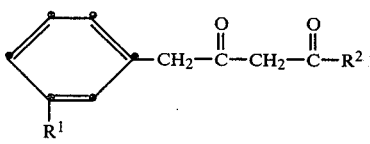

the first step is the formylation or aminoformylation of one of the methylene groups. If a formylating agent is used, a ketone of the formula

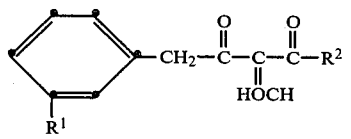

is produced. Reaction with an aminoformylating agent produces an enaminone such as (III) below.

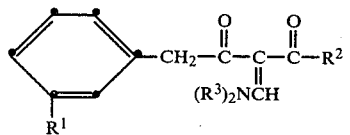

It is interesting to note that the insertion of the formyl or aminoformyl group, especially the aminoformyl group, is quite selective. It has been found that, when only one mole of aminoformylating agent is reacted with a mole of ketone, the resulting product is very predominately a single mono-aminoformyl compound, and not a mixture of the two possible mono-aminoformyl compounds.

The monosubstituted product is formylated or aminoformylated again, and exchanged with an amine of the formula $RNH_2$. The steps may be performed in either order. If the exchange is performed first, the intermediate product is of the formula

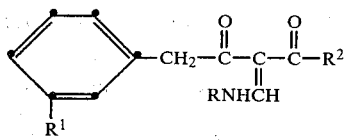

Either formylation or aminoformylation of the above enaminone affords the pyridinone product, as the intermediate cyclizes as soon as the second group is introduced on the other methylene group.

Alternatively, either of compounds (II) or (III) may be either formylated or aminoformylated to provide intermediates of any of the formulae below.

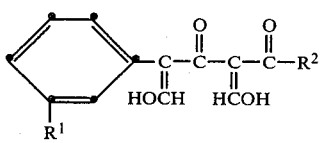

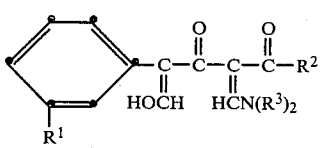

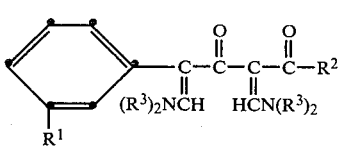

It will be understood that the compound similar to (VI), wherein the formyl and aminoformyl groups are reversed, is equivalent in all respects to compound (VI). Pyridinones are formed from any of the above three intermediates by simple contact of the intermediate with an amine of the formula $RNH_2$.

The compounds may also be prepared from carbonyl halides by a process essentially as described above, except for a first step performed as follows:

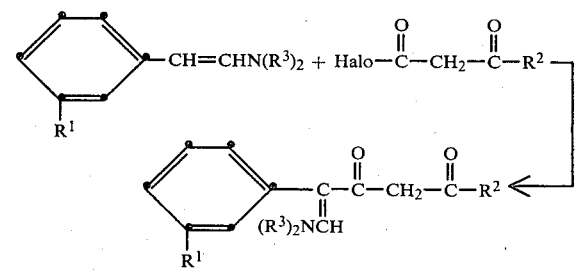

The enaminones formed above are converted to the pyridinone products as described above.

Alternatively, it is possible to prepare the 1-unsubstituted pyridinones by using $NH_3$ in place of $RNH_2$ in the process. The pyridinone is then alkylated at the 1-position with a halide of R, or with a dialkyl sulfate, according to common procedures.

As a chemist would expect, the amines, $RNH_2$, may be used in the form of salts, preferably hydrohalide salts, including hydrochlorides, hydrobromides and the like. Such salts are often more convenient than the free amines.

The formylating agents used in the process are chosen from the common agents used for such reactions. The preferred formylating agents are esters of formic acid of the formulae

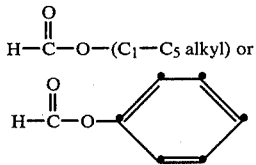

Similar formylations are discussed in Organic Syntheses 300-02 (Collective Vol. III 1955).

The esters are used in the presence of strong bases, of which alkali metal alkoxides are preferred, such as sodium methoxide, potassium ethoxide and lithium propoxide. Other bases may also be used, including alkali metal hydrides, alkali metal amides, and inorganic bases including alkali metal carbonates and hydroxides. Such strong organic bases as diazabicyclononane and diazabicycloundecane are also useful.

Reactions with formylating agents are performed in aprotic solvents such as are regularly used in chemical synthesis. Diethyl ether is usually the preferred solvent. Ethers in general, including solvents such as ethyl propyl ether, ethyl butyl ether, 1,2-dimethoxyethane and tetrahydrofuran, aromatic solvents such as benzene and xylene, and alkanes such as hexane and octane can be used as formylation solvents.

Because of the strong bases used in the formylation reactions, low temperatures produce the best yields. Reaction at temperatures in the range of from about $-25°$ to about $10°$ is preferred. The reaction mixture may be allowed to warm to room temperature, however, after the reaction has proceeded part way to completion. Reaction times from about 1 to about 24 hours are adequate for economic yields in the formylation reactions.

The aminoformylating agents used in these syntheses may be any compounds capable of reacting with an active methylene group to introduce a $=CHN(R^3)_2$ group, or its acid addition salt. Such agents are chosen from among s-triazine, the orthoformamides, $$HC[N(R^3)_2]_3$$

the formate ester animals,

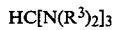

the formamide acetals,

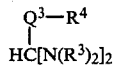

the tris(formylamino)methanes,

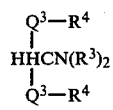

and preferably from the formiminium halides,

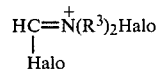

$Q^3$ in the structures above represents oxygen or sulfur, and $R^4$ represents $C_1$-$C_6$ alkyl or phenyl.

Useful references on the aminoformylating agents include DeWolfe, Carboxylic Acid Derivatives 420–506 (Academic Press 1970), and Ulrich, Chemistry of Imidoyl Halides 87–96 (Plenum Press 1968). Bredereck et al. have written many papers on such agents and reactions, of which the following are typical. Ber. 101, 4048–56 (1968); Ber. 104, 2709–26 (1971); Ber. 106, 3732–42 (1973); Ber. 97, 3397–406 (1964); Ann. 762, 62–72 (1972); Ber. 97, 3407–17 (1964); Ber. 103, 210–21 (1970); Angew. Chem. 78, 147 (1966); Ber. 98, 2887–96 (1965); Ber. 96, 1505–14 (1963); Ber. 104, 3475–85 (1971); Ber. 101, 41–50 (1968); Ber. 106, 3725–31 (1973); and Angew. Chem. Int'l. Ed. 5, 132 (1966). Other notable papers on the subject include Kreutzberger et al., Arch. der Pharm. 301, 881–96 (1968); and 302, 362–75 (1969); Weingarten et al., J. Org. Chem. 32, 3293–94 (1967); and Abdulla and Brinkmeyer, Tetrahedron 35, 1675 (1979).

Aminoformylations are usually carried out without solvent, at elevated temperatures from about 50° to about 150°. Solvents such as dimethylformamide are sometimes used, however, particularly when it is desirable to raise the boiling point of the reaction mixture.

When aminoformylating with formiminium halides, however, aprotic solvents, such as described above in the description of solvents for formylation, are used at temperatures from about 0° to about 80°, preferably above room temperature. Halogenated solvents such as chloroform and methylene chloride can also be used in such aminoformylations if desired.

The exchange reactions with $RNH_2$ are best performed in protic solvents of which alkanols are preferred and ethanol is most appropriate. Temperatures from about $-20°$ to about $100°$ can be used for the exchange reactions. Room temperature is satisfactory and is preferred.

In general, intermediate compounds in the synthesis are not purified, but are simply used in successive steps after separation by extraction, neutralization or removal of excess solvent or reactant as appropriate.

The enamine acylation reactions are performed in the presence of bases such as tertiary amines, alkali metal carbonates, magnesium oxide and the like, and in aprotic solvents as described above.

In some instances, as organic chemists will understand, it is necessary to apply additional synthetic steps after the pyridinone compound has been formed. Those compounds wherein the $R^2$ group is haloalkyl are best prepared by preparing the corresponding compound where $R^2$ is alkyl, and then halogenating in a second step with reagents such as N-chlorosuccinimide, N-bromophthalimide and the like. The examples below illustrate such preparations, which follow conventional halogenation procedures.

Most of the diketones which are the starting materials for the compounds of this invention are easily prepared by the condensation of a methyl phenylacetate with a methyl ketone, according to the following scheme.

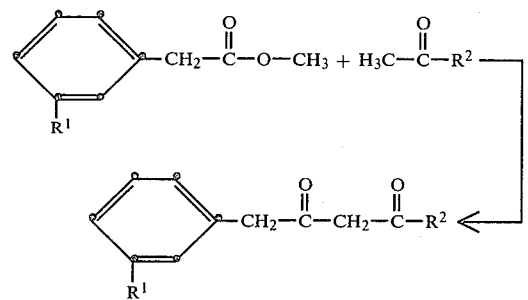

The reaction above is preferably carried out as described by Mühlemann, Pharm. Acta. Helv. 24, 376 (1949).

However, when $R^2$ is a phenyl or substituted phenyl group, the starting compound is preferably prepared as shown below.

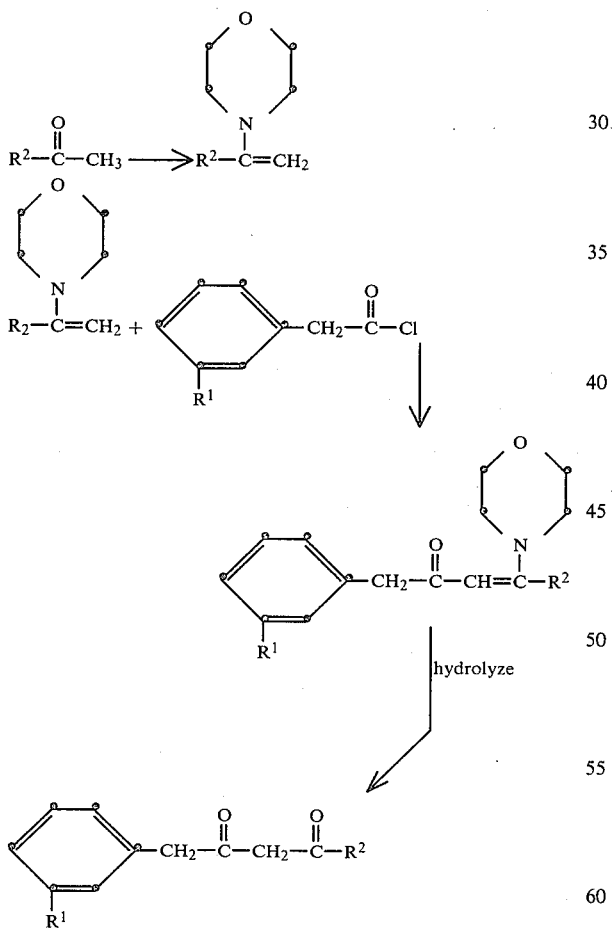

The first step of the above scheme is readily accomplished by refluxing the starting compound with excess morpholine in toluene with a catalytic amount of p-toluenesulfonic acid. The second step is preferably performed in an inert organic solvent such as diethyl ether in the presence of at least an equivalent amount of an acid scavenger, preferably triethylamine. The desired diketone starting compound is obtained from the morpholino intermediate by simple hydrolysis in the third step. Hydrolysis in acidic diethyl ether at ambient temperature has been found to be effective.

The starting compounds for those compounds of this invention wherein $R^2$ is tertiary alkyl, or alkoxyalkyl, are best prepared by a third scheme, illustrated below.

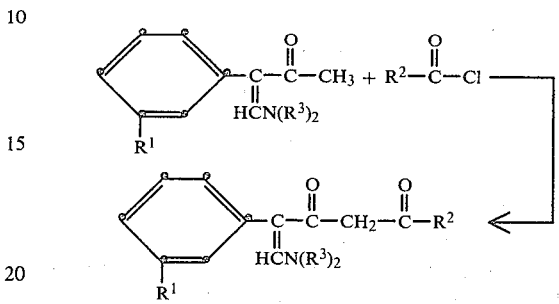

The intermediate above will be recognized as the general intermediate compound described first above, where $Q^1$ is an aminoformyl group, and $Q^2$ is two hydrogen atoms. In the scheme above, the acylation is carried out by first forming an anion of the enaminone starting compound by contact with a strong base such as n-butyllithium in the presence of diisoproplamine at a very low temperature. Operation at $-80°$ in tetrahydrofuran is preferred. The anion is smoothly acylated at the low temperature to form the needed starting compound.

All of the reactions described above proceed well without unusual excesses of any reactant. The stoichiometric amounts are adequate in all cases. As usual in organic chemistry, it is most economical to use a small excess, such as 1–20%, of inexpensive reagents to assure that more expensive ones are fully used.

The following preparations and examples further illustrate the methods by which the compounds of this invention are made. The products of the following procedures were usually identified by instrumental analytical methods, such as 60 mHz nuclear magnetic resonance with a tetramethylsilane internal standard (nmr), infrared (ir), and mass spectroscopy (ms).

The preparations immediately below show typical methods of preparing diketone starting compounds.

PREPARATION 1

1-(3-Trifluoromethylpheny)-2,4-pentanedione

Four hundred ml. of diethyl ether was dried over 4A molecular sieves, and to it was added 40 g. of sodium amide under nitrogen at 5°. The solution was warmed to 30°, and to it was added a mixture of 116 g. of ethyl 3-trifluoromethylphenylacetate and 40 g. of acetone. The addition was dropwise over 1 hour. A vigorous reflux occurred during the addition, which was controlled by the slow rate of addition. After the addition was over, the mixture was stirred for 4 hours, and was then dumped into 1.5 liters of ice-water. The aqueous mixture was extracted twice with 1-liter portions of diethyl ether, and was then adjusted to pH 5 with dilute hydrochloric acid. The pH was then taken back to 7.5 with sodium bicarbonate solution, and the mixture was extracted 3 times with 800 ml. portions of diethyl ether. The organic extracts were combined, dried over magnesium sulfate, and evaporated under vacuum to obtain 55 g. of viscous oil, which was distilled at 109°–110° at 0.4 Torr to obtain 22 g. of the desired product.

PREPARATION 2

1-Phenyl-4-(3-trifluoromethylphenyl)-1,3-butanedione

To 60 g. of acetophenone in 300 ml. of toluene was added 50 g. of morpholine and 0.2 g. of p-toluenesulfonic acid. The mixture was heated under vigorous reflux under a Dean-Stark condenser for 48 hours, during which time 9 ml. of water was separated. The mixture was then cooled and evaporated under vacuum to dryness, and the residue was taken up in 500 ml. of dichloromethane. The solution was washed with saturated aqueous sodium bicarbonate, dried over magnesium sulfate and evaporated under vacuum to a thick liquid, amounting to approximately 100 g. of crude α-morpholinostyrene, which was distilled at 85°–86° at 0.2 Torr to obtain 28.3 g. of intermediate product.

A 3.78 g. portion of the above intermediate was added to 25 ml. of benzene and to the solution was added with stirring a solution of 3-trifluoromethylphenylacetyl chloride in 25 ml. of benzene, over 1 hour. The reaction mixture was then stirred under reflux for 2 hours, and was chromatographed on 365 g. of silica gel with 5% ethyl acetate in toluene, increasing the ethyl acetate to 20% in stages. The fractions containing the desired product, B 1-morpholino-1-phenyl-4-(3-trifluoromethylphenyl)-3-oxo-1-butene, were collected and combined.

The above product, amounting to about 2 g. of oil, was dissolved in 100 ml. of benzene and was stirred under reflux for 2 hours with 40 ml. of 10% hydrochloric acid. The mixture was then washed with saturated sodium chloride solution, dried over magnesium sulfate and evaporated to dryness to obtain 1.5 g. of the desired intermediate product.

PREPARATION 3

6,6-Dimethyl-1-dimethylamino-2-(3-trifluoromethylphenyl)-1-heptene-3,5-dione

In 175 ml. of dry tetrahydrofuran was dissolved 3.9 g. of diisopropylamine with stirring under nitrogen. The solution was cooled to −65°, and 16 ml. of 2.4 molar n-butyllithium in hexane was added dropwise. The solution was stirred at constant temperature for 40 minutes, and to it was added dropwise 10 g. of 1-dimethylamino-2-(3-trifluoromethylphenyl)-1-butene-3-one dissolved in 50 ml. of tetrahydrofuran, and 25 ml. of hexamethylphosphoramide. The temperature at the end of the addition was −70°. The mixture was stirred for 1 hour at constant temperature and then 4.7 g. of pivaloyl chloride dissolved in 25 ml. of tetrahydrofuran was added dropwise. The mixture was stirred overnight and allowed to warm to ambient temperature. To the mixture was then added saturated potassium dihydrogen phosphate solution to bring its pH to 6, and the quenched reaction mixture was then partitioned between water and diethyl ether. The organic layer was dried over magnesium sulfate and evaporated under vacuum to obtain a dark oil, which was chromatographed on 300 g. of silica gel, eluting with 20% ethyl acetate in dichloromethane. The yield was 3.6 g. of the desired intermediate product.

EXAMPLE 1

3-Benzoyl-1-methyl-5-(3-trifluoromethylphenyl)-4(1H)-pyridinone

To a 9 g. portion of 1-phenyl-4-(3-trifluoromethylphenyl)-1,3-butanedione was added 60 ml. of N,N-dimethylformamide dimethyl acetal. The reaction mixture was stirred under reflux for 16 hours, and was then evaporated to a dark brown oil under vacuum. The oil was dissolved in 150 ml. of tetrahydrofuran, and to it was added 10 ml. of 40% aqueous methylamine. The mixture was allowed to stand at ambient temperature for 18 hours, and was then evaporated under vacuum to an oil, which was taken up in diethyl ether, washed with saturated sodium chloride solution, dried over magnesium sulfate and evaporated under vacuum to an oil again. The oil was triturated under 1.2 liters of diisopropyl ether to obtain 2.4 g. of the desired product, which was identified by nmr analysis in $CDCl_3$, showing characteristic peaks at δ7.2–8.0 (m, 11H, aromatic); 3.63 (s, 3H, N—$CH_3$).

EXAMPLE 2

1-Methyl-3-(3-trifluoromethylbenzoyl)-5-(3-trifluoromethylphenyl)-4(1H)-pyridinone A portion of 1-morpholino-1,4-bis(3-trifluoromethylphenyl)-1-butene-3-one was prepared as shown above in Preparation 2 from 10 g. of α-morpholino-3-trifluoromethylstyrene and 8.6 g. of 3-trifluoromethylphenylacetyl chloride. The resulting impure intermediate product, amounting to 12 g., was stirred under reflux with N,N-dimethylformamide dimethyl acetal and reacted with 10 ml. of aqueous methylamine, as described in Example 1 above. The product was purified according to the process of Example 1 to obtain 4.6 g. of the desired product, m.p. 115°–116°, showing nmr peaks in $CDCl_3$ at δ7.2–8.2 (m, 10H, aromatic); 6.70 (s, 3H, N—$CH_3$).

EXAMPLE 3

3-Acetyl-5-(3-chlorophenyl)-1-methyl-4(1H)-pyridinone

A 2.5 g. portion of 1-(3-chlorophenyl)-2,4-pentanedione was added to 30 ml. of N,N-dimethylformamide dimethyl acetal, and the mixture was stirred at reflux temperature for 18 hours. The reaction mixture was then evaporated to an oil under vacuum.

The oil was taken up in 150 ml. of tetrahydrofuran, and 10 ml. of 40% aqueous methylamine was added. The mixture was stirred at room temperature overnight, and evaporated under vacuum. The residue was dissolved in dichloromethane and precipitated by addition of hexane. The dried solids were chromatographed on silica gel by elution with ethyl acetate. The product-containing fractions were combined and evaporated to dryness under vacuum, and the isolated product was recrystallized from dichloromethane/hexane. A yield of 1.6 g. of the desired product, m.p. 175°–177°, was obtained. Nmr analysis in $DMSOd_6$ showed peaks at δ7.3–8.3 (m, 6H, aromatic); 3.80 (s, 3H, N—$CH_3$; 2.56 (s, 3H, $COCH_3$).

EXAMPLE 4

3-Acetyl-5-(3-bromophenyl)-1-methyl-4(1H)-pyridinone

To 1.5 g. of 1-(3-bromophenyl)-2,4-pentanedione was added 25 ml. of N,N-dimethylformamide dimethyl acetal. The mixture was stirred at reflux temperature for 18 hours, cooled and evaporated to a thick oil under vacuum. The oil was dissolved in 500 ml. of tetrahydrofuran, and 10 ml. of 40% aqueous methylamine was added. The mixture was stirred at ambient temperature for 4 hours, and was then evaporated under vacuum. The residue was dissolved in 800 ml. of dichloromethane, and washed with 500 ml. of water. The organic layer was dried over magnesium sulfate, treated with activated charcoal, filtered and evaporated under vacuum. The solids were recrystallized twice from dichloromethane/diisopropyl ether. The solids were then chromatographed on a silica gel column with ethyl acetate as the eluting solvent. The yield was 0.8 g. of the desired product, m.p. 192°–194°. Nmr analysis in DMSOd$_6$ showed peaks at δ7.25–8.40 (m, 6H, aromatic); 3.75 (s, 3H, N—CH$_3$); 2.53 (s, 3H, COCH$_3$).

EXAMPLE 5

3-Acetyl-5-(3-fluorophenyl)-1-methyl-4(1H)-pyridinone

A 1.5 g. portion of 1-(3-fluorophenyl)-2,4-pentanedione was reacted with 15 ml. of N,N-dimethylformamide dimethyl acetal, and then with 10 ml. of 40% aqueous methylamine as described in Example 4. The reaction mixture was then evaporated under vacuum to dryness, and the crude product was chromatographed on a silica gel column with ethyl acetate to obtain 1 g. of the desired product, which was identified by nmr analysis in CDCl$_3$, showing peaks at δ8.1–8.2 (m, 1H, pyridine); 6.9–7.6 (m, 5H, phenyl and 1 pyridine); 3.80 (s, 3H, N—CH$_3$); 2.83 (s, 3H, COCH$_3$).

EXAMPLE 6

1-Methyl-3-propionyl-5-(3-trifluoromethylphenyl)-4(1H)-pyridinone

A 29.1 g. portion of 1-(3-trifluoromethylphenyl)-2,4-hexanedione was combined with 120 ml. of N,N-dimethylformamide dimethyl acetal and the mixture was stirred under reflux overnight. The mixture was then evaporated to a thick dark brown oil under vacuum, and the residue was dissolved in 250 ml. of methanol. Forty g. of methylamine hydrochloride was added and the mixture was stirred under reflux for 2 hours, and at ambient temperature for 60 hours. The mixture was then evaporated under vacuum to dryness, and the residue was taken up in water and diethyl ether. The organic layer was dried over magnesium sulfate and evaporated under dryness to a dark brown solid, which was chromatographed on a 500 g. silica gel column with ethyl acetate as the eluting solvent. The product-containing fractions were combined and evaporated under vacuum to obtain a light orange solid, which was crystallized from diisopropyl ether to obtain 3.04 g. of the desired product, m.p. 136°–138°. Nmr analysis in DMSOd$_6$ showed peaks at δ7.6–8.3 (m, 6H, aromatic); 3.8 (s, 3H, N—CH$_3$); 2.9–3.3 (q, 2H, CO$\underline{\text{CH}}_2$CH$_3$); 0.9–1.1 (t, 3H, COCH$_2\underline{\text{CH}}_3$).

EXAMPLE 7

3-Acetyl-1-methyl-5-(3-trifluoromethylphenyl)-4(1H)-pyridinone

Ten g. of 1-(3-trifluoromethylphenyl)-2,4-pentanedione was reacted with 40 ml. of N,N-dimethylformamide dimethyl acetal, and then with 10 ml. of 40% aqueous methylamine, as described in the examples above. The reaction mixture was evaporated under vacuum, and the residue was taken up in 1.5 liters of dichloromethane. The solution was washed with 1 liter of water, and the organic layer was dried with magnesium sulfate, treated with activated charcoal, filtered and evaporated under vacuum. The residue was triturated under diisopropyl ether, and a yellow powdery solid crystallized. The solid was found to be 4.56 g. of the desired product, m.p. 130°–131°, showing the following peaks in nmr analysis: δ8.10 (d, J=3 Hz, H2 of pyridine); 8.0–7.3 (m, 4H, aromatic); 7.43 (d, J=3 Hz, H6 of pyridine); 3.77 (s, 3H, N—CH$_3$); 2.73 (s, 3H, COCH$_3$).

The following example shows an alternate order of the steps which produce the above compound.

EXAMPLE 8

3-Acetyl-1-methyl-5-(3-trifluoromethylphenyl)-4(1H)-pyridinone

To 5 g. of 1-(3-trifluoromethylphenyl)-2,4-pentanedione was added 2.4 g. of N,N-dimethylformamide dimethyl acetal, and the mixture was stirred at ambient temperature for 16 hours. The reaction mixture was evaporated under vacuum to obtain 6 g. of crude 3-dimethylaminomethylene-1-(3-trifluoromethylphenyl)-2,4-pentanedione, which was identified by nmr analysis.

A 3.9 g. portion of the above intermediate product was dissolved in 25 ml. of methanol, and to it was added 15 ml. of 40% aqueous methylamine. The mixture was stirred at ambient temperature for 1.5 hours, and was evaporated under vacuum. The residue was identified by nmr analysis as impure 3-methylaminomethylene-1-(3-trifluoromethylphenyl)-2,4-pentanedione.

To 3.9 g. of the above impure intermediate in 25 ml. of toluene was added 1.8 g. of dimethylformamide dimethyl acetal, and the mixture was stirred at reflux overnight. The mixture was evaporated under vacuum to obtain 4.3 g. of pyridinone in crude form, which was chromatographed with ethyl acetate on a 350 g. silica gel column. The product-containing fractions were combined and evaporated under vacuum. The residue was triturated under diisopropyl ether to obtain a small portion of the desired product, identical to the product of Example 7 above.

EXAMPLE 9

3-Acetyl-1-ethyl-5-(3-trifluoromethylphenyl)-4(1H)-pyridinone

The process of Example 8 was followed, except that the amine reactant was 10 ml. of 70% aqueous ethylamine. The final product was purified by chromatography substantially as was the product of Example 8. The product was 0.9 g. of the desired compund in rather impure form. Nmr analysis in DMSOd$_6$ showed peaks at δ7.5–8.4 (m, 6H, aromatic); 4.0–4.4 (q, 2H, N—CH$_2$); 2.6 (s, 3H, COCH$_3$); 1.3–1.6 (t, 3H, CH$_2$CH$_3$).

EXAMPLE 10

3-Butyryl-1-methyl-5-(3-trifluoromethylphenyl)-4(1H)-pyridinone

A mixture of 1.6 g. of 1-(3-trifluoromethylphenyl)-2,4-heptanedione and 50 ml. of N,N-dimethylformamide dimethyl acetal was stirred for 3 hours at reflux temperature, and then at ambient temperature overnight. The mixture was evaporated under vacuum to obtain 2.3 g. of a thick dark oil, which was dissolved in 25 ml. of methanol. Five g. of methylamine hydrochloride was added, and the mixture was stirred under reflux for 2 hours and then at ambient temperature overnight. The mixture was then evaporated under vacuum, and the residue was partitioned between diethyl ether and water. The organic layer was dried over magnesium sulfate and evaporated under vacuum to obtain a thick brown oil, which was chromatographed on a 300 g. silica gel column with 2:3 ethyl acetate:dichloromethane. The product-containing fractions were combined, and the product crystallized from the solvent on standing. The product was collected and triturated under hexane to obtain 0.19 g. of the desired product, m.p. 93°–94°. Nmr analysis in DMSOd$_6$ showed peaks at δ7.6–8.3 (m, 6H, aromatic); 3.9 (s, 3H, N—CH$_3$); 3.0–3.2 (t, 2H, COCH$_2$); 1.3–1.9 (m, 2H, C$\underline{H}_2$CH$_3$); 0.8–1.1 (t, 3H, CH$_2$C$\underline{H}_3$).

EXAMPLE 11

3-Isobutyryl-1-methyl-5-(3-trifluoromethylphenyl)-4(1H)-pyridinone

A 0.6 g. portion of impure 5-methyl-1-(3-trifluoromethylphenyl)-2,4-hexanedione was reacted overnight at reflux temperature with N,N-dimethylformamide dimethyl acetal as described in the examples above to obtain 0.8 g. of a dark oil. The oil was dissolved in methanol and reacted with 2 g. of methylamine hydrochloride under reflux for 4 hours. The reaction mixture was evaporated under vacuum to obtain a yellow solid, which was purified as described in Example 10 to obtain 0.09 g. of the desired product, m.p. 104°–105°, showing the following peaks in nmr analysis in DMSOd$_6$: δ7.6–8.3 (m, 6H, aromatic); 3.7–4.2 (m, 1H, COCH); 3.8 (s, 3H, N—CH$_3$); 1.0–1.2 (d, 6H, CH(C$\underline{H}_3$)$_2$).

EXAMPLE 12

1-Methyl-3-(3-trifluoromethylphenyl)-5-valeryl-4(1H)-pyridinone

To a 6 g. portion of crude 1-(3-trifluoromethylphenyl)-2,4-octanedione was added 40 ml. of N,N-dimethylformamide dimethyl acetal and a few milliliters of methanol. The mixture was stirred under reflux overnight, and was then evaporated under vacuum to obtain 8.9 g. of a thick dark oil. The oil was taken up in 50 ml. of methanol, 9 g. of methylamine hydrochloride was added, and the mixture was stirred under reflux for 3 hours. It was then evaporated to a semi-solid under vacuum, and the residue was partitioned between diethyl ether and water. The organic layer was dried over magnesium sulfate and evaporated under vacuum. The residue was chromatographed on a 300 g. silica gel column with 2:3 ethyl acetate:dichloromethane, and the product-containing fractions were combined and evaporated under vacuum to obtain 0.17 g. of the desired product in impure form. Nmr analysis in DMSOd$_6$ showed peaks at δ7.6–8.3 (m, 6H, aromatic); 3.8 (s, 3H, N—CH$_3$); 3.0–3.3 (t, 2H, COCH$_2$); 0.7–1.8 (m, 7H, CH$_2$CH$_2$CH$_3$).

EXAMPLE 13

1-Methyl-3-(2-methylbutyryl)-5-(3-trifluoromethylphenyl)-4(1H)-pyridinone

A 1.3 g. portion of impure 5-methyl-1-(3-trifluoromethylphenyl)-2,4-heptanedione was reacted with 50 ml. of N,N-dimethylformamide dimethyl acetal, and then with 2 g. of methylamine hydrochloride as described in Example 12. The impure product was purified as described in Example 12, except that the final product was subjected to an additional step of trituration under hexane to obtain 0.08 g. of the desired product, m.p. 109°–111°, showing the following nmr peaks in CDCl$_3$: δ7.3–8.1 (m, 6H, aromatic); 3.9–4.2 (m, 1H, COCH); 3.8 (s, 3H, N—CH$_3$); 1.2–2.0 (m, 2H, C$\underline{H}_2$CH$_3$); 1.1–1.2 (d, 3H, CHC$\underline{H}_3$); 0.8–1.1 (t, 3H, CH$_2$C$\underline{H}_3$).

EXAMPLE 14

1-Methyl-3-(3-methylbutyryl)-5-(3-trifluoromethylphenyl)-4(1H)-pyridinone

A 3.9 g. portion of impure 6-methyl-1-(3-trifluoromethylphenyl)-2,4-heptanedione was reacted with 50 ml. of N,N-dimethylformamide dimethyl acetal, and then with 5 g. of methylamine hydrochloride as described in the examples above. The product was purified as described in Example 13 to obtain 0.22 g. of the desired product, m.p. 110°–112°. Nmr analysis is DMSOd$_6$ showed peaks at δ7.6–8.3 (m, 6H, atomic); 3.8 (s, 3H, N—CH$_3$); 2.9–3.1 (d, 2H, COCH$_2$); 1.8–2.4 (m, 1H, CH$_2$C$\underline{H}$); 0.8–1.0 (d, 6H, CH(C$\underline{H}_3$)$_2$).

EXAMPLE 15

1-Methyl-3-(2,2-dimethylpropionyl)-5-(3-trifluoromethylphenyl)-4(1H)-pyridinone

The product of Preparation 3 above, 3.6 g. of impure 6,6-dimethyl-1-dimethylamino-2-(3-trifluoromethylphenyl)-1-heptene-3,5-dione, was dissolved in 17 ml. of N,N-dimethylformamide dimethyl acetal and stirred under reflux at about 100° overnight using a sub-surface nitrogen bubbler. The mixture was then evaporated under vacuum to obtain 3.5 g. of a dark oil, which was dissolved in 120 ml. of tetrahydrofuran and reacted with 15 ml. of 40% aqueous methylamine at ambient temperature for 1 hour. The mixture was then evaporated under vacuum, and the resulting oil was chromatographed on a 300 g. silica gel column with 2:3 ethyl acetate:dichloromethane as the eluting solvent. The product-containing fractions was combined and evaporated under vacuum, and the residue was triturated under hexane to obtain 0.6 g. of the desired product, m.p. 86°–88°, showing the following peaks on nmr analysis in DMSOd$_6$: δ7.6–8.2 (m, 6H, aromatic); 3.8 (s, 3H, N—CH$_3$); 1.2 (s, 9H, C(C$\underline{H}_3$)$_3$).

EXAMPLE 16

3-Methoxyacetyl-1-methyl-5-(3-trifluoromethylphenyl)-4(1H)-pyridinone

A 1 g. portion of impure 1-dimethylamino-6-methoxy-2-(3-trifluoromethylphenyl)-1-hexene-3,5-dione was reacted with 10 ml. of N,N-dimethylformamide dimethyl acetal, and then with 5 ml. of 40% aqueous methylamine, as described in Example 15. The product was purified as described in that example, except that 1:1 ethyl acetate:dichloromethane was used as the eluent, to obtain 0.13 g. of the desired product, m.p. 140°, dec. Nmr analysis in DMSOd$_6$ showed peaks at δ7.6–8.5 (m, 6H, aromatic); 4.8 (s, 2H, COCH$_2$); 3.9 (s, 3H, N—CH$_3$); 3.4 (s, 3H, OCH$_3$).

EXAMPLE 17

3-Dichloroacetyl-1-ethyl-5-(3-trifluoromethylphenyl)-4(1H)-pyridinone

A 0.9 g. portion of 3-acetyl-1-ethyl-5-(3-trifluoromethylphenyl)-4(1H)-pyridinone was combined with 0.8 g. of N-chlorosuccinimide in 125 ml. of chloroform. The mixture was stirred at reflux overnight, and was then cooled, washed with 1 N sodium hydroxide solution and then with saturated sodium chloride solution, and evaporated under vacuum to obtain 0.9 g. of an orange glass. The residue was chromatographed on a 350 g. silica gel column with 1:10 ethyl acetate:chloroform as the eluting solvent. The product-containing fractions were combined and evaporated under vacuum. The residue was then triturated under hexane to obtain 0.25 g. of the desired product, m.p. 108°–110°. Nmr analysis in DMSOd$_6$ showed peaks at δ7.6–8.4 (m, 7H, aromatic and CHCl$_2$); 4.0–4.4 (q, 2H, N—CH$_2$); 1.4–1.6 (t, 3H, CH$_2$CH$_3$).

EXAMPLE 18

3-Dichloroacetyl-5-(3-chlorophenyl)-1-methyl-4(1H)-pyridinone

A 1.1 g. portion of 3-acetyl-5-(3-chlorophenyl)-1-methyl-4(1H)-pyridinone was dissolved in 100 ml. of dichloromethane, and to it was added dropwise a solution of 1.06 g. of N-chlorosuccinimide in 50 ml. of dichloromethane. After the addition, the reaction mixture was stirred at reflux for 2 days, during which time two additional 0.5 g. portions of N-chlorosuccinimide were added. The mixture was then cooled, diluted with additional dichloromethane, and washed twice with 2 N sodium hydroxide solution. The organic portion was dried over magnesium sulfate, filtered and evaporated under vacuum. The residue was recrystallized from dichloromethane/hexane to obtain 0.4 g. of the desired product, m.p. 201°–202°. Nmr analysis in DMSOd$_6$ showed peaks at δ8.50–8.55 (d, 1H, pyridine); 8.10–8.16 (d, 1H, pyridine); 7.3–8.8 (m, 5H, aromatic and CHCl$_2$); 3.81 (s, 3H, N—CH$_3$).

EXAMPLE 19

3-Dichloroacetyl-5-(3-fluorophenyl)-1-methyl-4(1H)-pyridinone

A 1 g. portion of 3-acetyl-5-(3-fluorophenyl)-1-methyl-4(1H)-pyridinone was reacted with 1.06 g. of N-chlorosuccinimide as described in Example 18. The product was 0.3 g. of the desired product, m.p. 183°–184°. Nmr analysis in CDCl$_3$ showed peaks at δ7.16–8.56 (m, 7H, aromatic and CHCl$_2$); 3.85 (s, 3H, N—CH$_3$).

EXAMPLE 20

3-(2-Chloropropionyl)-1-methyl-5-(3-trifluoromethylphenyl)-4(1H)-pyridinone

A 2.7 g. portion of 1-methyl-3-propionyl-5-(3-trifluoromethylphenyl)-4(1H)-pyridinone was dissolved in 125 ml. of chloroform, and 2.3 g. of N-chlorosuccinimide was added. The mixture was stirred under reflux overnight, and was then cooled and washed, first with 1 N sodium hydroxide, and then with saturated sodium chloride solution. The organic layer was then dried over magnesium sulfate and evaporated under vacuum to obtain 2.2 g. of a partially crystalline solid. The product was crystallized from diisopropyl ether to obtain 1.2 g. of the desired product, m.p. 129°, dec., showing the following nmr peaks in DMSOd$_6$: δ7.5–8.4 (m, 6H, aromatic); 5.8–6.2 (q, 1H, CHCl); 1.5–1.6 (d, 3H, CHClCH$_3$); 3.8 (s, 3H, N—CH$_3$).

EXAMPLE 21

3-Chloroacetyl-1-methyl-5-(3-trifluoromethylphenyl)-4(1H)-pyridinone

EXAMPLE 22

3-Dichloroacetyl-1-methyl-5-(3-trifluoromethylphenyl)-4(1H)-pyridinone

A 4.5 g. portion of 3-acetyl-1-methyl-5-(3-trifluoromethylphenyl)-4(1H)-pyridinone was dissolved in 125 ml. of dichloromethane, and 2 g. of N-chlorosuccinimide was added. The mixture was stirred under reflux for 60 hours. The mixture was then cooled, and washed successively with 150 ml. each of 1 N sodium hydroxide, 1 N hydrochloric acid, and saturated sodium chloride solution. It was then dried over magnesium sulfate, and evaporated under vacuum to obtain a tan solid. The residue was chromatographed on a 350 g. silica gel column, with 1:10 ethyl acetate:dichloromethane as the eluting solvent. The first product off the column was the dichloroacetyl compound of Example 22, m.p. 184°–186° C., of which 0.6 g. was obtained. Nmr analysis in DMSOd$_6$ showed the following peaks: δ8.4 (s, 1H, CHCl$_2$); 7.6–8.3 (m, 6H, aromatic); 3.9 (s, 3H, N—CH$_3$).

The second compound obtained was the monochloroacetyl compound of Example 21, m.p. 156°–158°, dec., of which 0.9 g. was obtained. Its nmr analysis in DMSOd$_6$ showed the following peaks: δ7.5–8.6 (m, 6H, aromatic); 5.1 (s, 2H, CH$_2$Cl); 3.9 (s, 3H, N—CH$_3$).

Representative compounds of this invention have been tested in herbicidal and algicidal test systems to determine the range of their efficacy. In the tests described below, the compound application rates are expressed in kilograms of the compound per hectare of land (kg./ha.), except where otherwise stated.

Blank spaces in the tables below indicate that the compound was not tested against the named species. In some instances, the results of testing a compound repeatedly against a plant species have been averaged.

Untreated control plants or pots were included in all tests. Ratings of the control produced by the compounds were made by comparison of the treated plants or plots with the controls.

In tests 1–3 below, the plants were rated on a 1–5 scale, on which 1 indicates normal plants and 5 indicates dead plants or no emergence. The plants in tests 4–5 below were rated as percent control of the plants.

TEST 1

Broad spectrum greenhouse test

Plastic pots were filled with a sterilized sandy loam soil and were planted to seeds of tomato, large crabgrass and pigweed. Each pot was individually fertilized.

Test compounds were applied preemergence to some plants and postemergence to others. Postemergence applications of the compounds were sprayed over the emerged plants about 12 days after the seeds were planted. Preemergence applications were sprayed on the soil the day after the seeds were planted.

Each test compound was dissolved in 1:1 acetone:ethanol at the rate of 2 g. per 100 ml. The solution also contained about 2 g. per 100 ml. of an anionic-nonionic surfactant blend. One ml. of the solution was diluted to 4 ml. with deionized water, and 1.5 ml. of the resulting solution was applied to each pot, providing an application rate of 16.8 kg./ha. of test compound.

After the compounds were applied, the pots were moved to the greenhouse, watered as necessary, and observed and rated 10–13 days after application of the compounds.

The table below reports results of testing typical compounds of the invention. The compounds are identified by their example numbers above.

TABLE 1

| Compound of Example No. | Preemergence | | | Postemergence | | |
|---|---|---|---|---|---|---|
| | Tomato | Large Crab-Grass | Pig-weed | Tomato | Large Crab-grass | Pig-weed |
| 1 | | | | | | |
| 2 | 2 | 4 | 4 | 2 | 2 | 2 |
| 4 | 4 | 4 | 4 | 3 | 3 | 2 |
| 5 | | | | | | |

TEST 2

7-Species Greenhouse Test

The test was conducted in general like the test described in Test 1, except that in this test the seeds were planted in flat metal trays, rather than in pots. The compounds were formulated according to the procedure described in Test 1, except that about 6 g./100 ml. of the compound was dissolved in the surfactant-containing solvent, and about 1 part of the organic solution was diluted with 12 parts of water before application to the trays. The compounds were applied at the rate of 9.0 kg./ha., and the results of testing representative compounds against the species named below were as follows.

TABLE 2

| Compound of Example No. | Preemergence | | | | | | | Postemergence | | | | | | |
|---|---|---|---|---|---|---|---|---|---|---|---|---|---|---|
| | Corn | Large Crab-grass | Pig-weed | Fox-tail | Velvet-leaf | Morning-glory | Zinnia | Corn | Large Crab-grass | Pigweed | Foxtail | Velvetleaf | Morning-glory | Zinnia |
| 1 | 2 | 4 | 4 | 3 | 3 | 2 | 2 | 1 | 1 | 2 | 1 | 1 | 1 | 2 |
| 2 | 1 | | 4 | 3 | 2 | 1 | 1 | 1 | 1 | 2 | 1 | 1 | 1 | 2 |
| 3 | 4 | 5 | 3 | 5 | 3 | 2 | 3 | 2 | 4 | 2 | 2 | 2 | 2 | 2 |
| 4 | 4 | 5 | 4 | 5 | 2 | 1 | 2 | 2 | 3 | 2 | 2 | 1 | 2 | 2 |
| 5 | | | | | | | | | | | | | | |
| 6 | 5 | 5 | 5 | 5 | 5 | 3 | 4 | 4 | 5 | 4 | 4 | 4 | 3 | 5 |
| 7 | 5 | 5 | 5 | 5 | 5 | 5 | 5 | 4 | 4 | 3 | 3 | 3 | 3 | 3 |
| 10 | 5 | 4 | 4 | 5 | 5 | 5 | 4 | 3 | 4 | 3 | 3 | 3 | 3 | 3 |
| 11 | 5 | 5 | 5 | 5 | 5 | 4 | 4 | 3 | 4 | 3 | 3 | 3 | 3 | 3 |
| 12 | 4 | 5 | 4 | 4 | 2 | 3 | 2 | 3 | 3 | 4 | 2 | 3 | 3 | 3 |
| 13 | 4 | 5 | 5 | 5 | 4 | 2 | 3 | 2 | 3 | 2 | 2 | 2 | 2 | 3 |
| 14 | 4 | 5 | 5 | 5 | 5 | 5 | 4 | 3 | 3 | 4 | 2 | 3 | 3 | 3 |
| 15 | 5 | 5 | 5 | 5 | 5 | 4 | 5 | 3 | 3 | 4 | 3 | 3 | 3 | 3 |
| 16 | 2 | 3 | 4 | 1 | 1 | 1 | 2 | 3 | 2 | 5 | 2 | 3 | 3 | 3 |
| 17 | 5 | 4 | 3 | 5 | 4 | 2 | 3 | 2 | 3 | 3 | 3 | 3 | 3 | 4 |
| 18 | 2 | 4 | 3 | 4 | 2 | 1 | 2 | 2 | 2 | 2 | 2 | 1 | 2 | 2 |
| 19 | 1 | 3 | 2 | 3 | 1 | 1 | 2 | 2 | 2 | 2 | 1 | 2 | 2 | 2 |
| 20 | 3 | 4 | 5 | 5 | 3 | 3 | 2 | 3 | 2 | 3 | 3 | 3 | 3 | 3 |
| 21 | 4 | 4 | 5 | 5 | 4 | 4 | 4 | 2 | 2 | 3 | 2 | 2 | 3 | 3 |
| 22 | 5 | 5 | 5 | 5 | 2 | 2 | 4 | 2 | 3 | 4 | 2 | 2 | 3 | 3 |
| 7 | | | | | | | | | | | | | | |
| 16 | 4 | 5 | 5 | 4 | 4 | 3 | | | | | | | | |
| 20 | 5 | 5 | 5 | 4 | 4 | 4 | | | | | | | | |
| 21 | 5 | 5 | 5 | 4 | 3 | 4 | | | | | | | | |
| 22 | 5 | 5 | 5 | 3 | 3 | 3 | | | | | | | | |

TEST 3

Multiple-Species Greenhouse Test

The tests reported below were carried out according to the method described in Test 2 above, except that the compounds were applied at the rate of 1.1 kg./ha. The preemergence tests are reported in Table 3 below, and the postemergence results, in Table 4.

TABLE 3

| Compound of Example No. | Preemergence | | | | | | | | | | |
|---|---|---|---|---|---|---|---|---|---|---|---|
| | Corn | Cotton | Soybean | Wheat | Alfalfa | Sugar Beet | Rice | Cucumber | Tomato | Barnyard Grass | Lambs-Quarter |
| 1 | 1 | 1 | 1 | 1 | 2 | 2 | 1 | 1 | 1 | 1 | 3 |
| 3 | 1 | 1 | 1 | 1 | 2 | 1 | 1 | 1 | 1 | 2 | 3 |
| 4 | 2 | 2 | 2 | 1 | 2 | 2 | 2 | 2 | 2 | 4 | 3 |
| 5 | | | | | | | | | | | |
| 6 | 4 | 1 | 4 | 4 | 2 | 5 | 4 | 4 | 5 | 4 | 5 |
| 7 | 2 | 1 | 2 | 4 | 3 | 3 | 2 | 2 | 3 | 4 | 4 |
| 10 | 4 | 1 | 4 | 4 | 4 | 5 | 3 | 2 | 4 | 4 | 5 |
| 11 | 4 | 1 | 2 | 4 | 3 | 4 | 2 | 2 | 2 | 4 | 4 |
| 12 | 2 | 1 | 1 | 1 | 1 | 2 | 1 | 2 | 1 | 3 | 4 |
| 13 | 3 | 1 | 2 | 2 | 2 | 4 | 1 | 2 | 1 | 3 | 5 |
| 14 | 4 | 1 | 2 | 2 | 2 | 4 | 2 | 1 | 1 | 2 | 4 |
| 15 | 2 | 1 | 2 | 1 | 3 | 4 | 2 | 2 | 3 | 3 | 5 |
| 17 | 1 | 1 | 1 | 1 | 1 | 1 | 1 | 1 | 1 | 2 | 2 |
| 18 | 1 | 1 | 1 | 1 | 2 | 1 | 1 | 1 | 1 | 1 | 1 |
| 20 | 2 | 1 | 2 | 1 | 2 | 4 | 2 | 2 | 1 | 2 | 4 |
| 21 | 2 | 1 | 1 | 2 | 2 | 3 | 3 | 2 | 2 | 4 | 4 |
| 22 | 1 | 1 | 2 | 1 | 2 | 2 | 1 | 2 | 2 | 2 | 4 |

Compound

TABLE 3-continued

| of Example No. | Preemergence | | | | | | | | |
|---|---|---|---|---|---|---|---|---|---|
| | Large Crabgrass | Mustard | Pigweed | Foxtail | Wild Oat | Velvetleaf | Jimsonweed | Morning-glory | Zinnia |
| 1 | 4 | 2 | 3 | 1 | 1 | 2 | 1 | 1 | 1 |
| 3 | 4 | 2 | 1 | 4 | 2 | 2 | 2 | 1 | 2 |
| 4 | 4 | 2 | 2 | 4 | 2 | 2 | 4 | 1 | 2 |
| 5 | | | | | | | | | |
| 6 | 4 | 4 | 4 | 5 | 5 | 5 | 4 | 4 | 5 |
| 7 | 5 | 5 | 4 | 5 | 4 | 4 | 3 | 4 | 4 |
| 10 | 5 | 4 | 5 | 5 | 4 | 4 | 4 | 4 | 4 |
| 11 | 5 | 3 | 4 | 4 | 4 | 3 | 3 | 2 | 2 |
| 12 | 4 | 2 | 4 | 4 | 3 | 2 | 2 | 2 | 1 |
| 13 | 5 | 3 | 3 | 4 | 2 | 4 | 2 | 2 | 1 |
| 14 | 3 | 2 | 4 | 3 | 5 | 1 | 1 | 1 | 4 |
| 15 | 4 | 3 | 2 | 4 | 4 | 5 | 4 | 2 | 2 |
| 17 | 4 | 1 | 1 | 1 | 2 | 1 | 1 | 1 | 1 |
| 18 | 2 | 2 | 2 | 1 | 1 | 1 | 1 | 1 | 1 |
| 20 | 5 | 3 | 2 | 5 | 3 | 3 | 4 | 2 | 2 |
| 21 | 4 | 2 | 4 | 4 | 2 | 2 | 2 | 2 | 2 |
| 22 | 4 | 2 | 2 | 4 | 2 | 2 | 2 | 1 | 2 |

TABLE 4

| Compound of Example No. | Corn | Foxtail Millet | Grain Sorghum | Wild Oat | Rice | Barnyard Grass | Wheat | Sugar Beets | Soy-bean | Velvet-leaf | Cotton | Pig-weed | Cucum-ber | Jimson-weed |
|---|---|---|---|---|---|---|---|---|---|---|---|---|---|---|
| 3 | 20 | 70 | 10 | 45 | 20 | 65 | 60 | 30 | 35 | 30 | 10 | 10 | 45 | 20 |
| 4 | 40 | 85 | 60 | 60 | 30 | 65 | 80 | 0 | 25 | 20 | 0 | 0 | 40 | 30 |
| 6* | 100 | 100 | 100 | 100 | 90 | 98 | 100 | 100 | 80 | 100 | 0 | 100 | 80 | 99 |
| 10* | 98 | 100 | 100 | 98 | 90 | 98 | 100 | 100 | 98 | 95 | 50 | 100 | 35 | 100 |
| 11 | 100 | 100 | 100 | 100 | 98 | 100 | 100 | 100 | 100 | 100 | 20 | 100 | 80 | 98 |
| 12 | 80 | 70 | 90 | 75 | 30 | 60 | 90 | 100 | 10 | 20 | 0 | 60 | 10 | 20 |
| 13 | 60 | 80 | 80 | 40 | 0 | 50 | 80 | 98 | 40 | 50 | 0 | 40 | 20 | 50 |
| 20 | 100 | 100 | 100 | 100 | 90 | 98 | 100 | 100 | | 100 | 20 | 100 | 95 | 100 |

*0.28 kg./ha.

| Compound of Example No. | Postemergence | | | | | | |
|---|---|---|---|---|---|---|---|
| | Corn | Large Crab-grass | Pig-weed | Fox-tail | Velvet-leaf | Morning-glory | Zin-nia |
| 6 | 3 | 4 | 3 | 3 | 3 | 3 | 3 |
| 7 | 2 | 2 | 2 | 2 | 2 | 3 | 2 |
| 16 | 2 | 2 | 3 | 2 | 3 | 3 | 2 |

TEST 4

Soil-Incorporated 14-Species Test

The tests reported below were performed to evaluate typical compounds of this invention against a number of crop and weed species. The compounds were formulated as described above under Test 1, except that the acetone-ethanol solution contained about 1 g./100 ml. of the test compound. The acetone-ethanol solution was appropriately diluted to allow convenient application at the rate of 1.1 kg./ha. In all cases, the compounds were applied preemergence to the test plants, and were incorporated in the soil before the seeds were planted.

TABLE 5

TEST 5

Fourteen-Species Greenhouse Test

The tests reported below were carried out as described under Test 4 except that the compounds were not incorporated in the soil, but were applied preemergence to the surface of the soil in the flat metal trays in which the plants were grown. The results of testing representative compounds at 1.1 kg./ha. are shown below in Table 6.

TABLE 6

| Compound of Example No. | Corn | Foxtail Millet | Grain Sorghum | Wild Oat | Rice | Barnyard Grass | Wheat | Sugar Beets | Soy-bean | Velvet-leaf | Cotton | Pig-weed | Cucum-ber | Jimson-weed |
|---|---|---|---|---|---|---|---|---|---|---|---|---|---|---|
| 3 | 0 | 80 | 0 | 0 | 0 | 0 | 0 | 0 | 10 | 0 | 0 | 20 | 10 | 20 |
| 4 | 10 | 95 | 0 | 10 | 0 | 50 | 0 | 0 | 5 | 0 | 0 | 0 | 0 | 0 |
| 6 | 100 | 100 | 70 | 70 | 70 | 100 | 70 | 90 | 80 | 100 | 0 | 100 | 80 | 100 |
| 10 | 100 | 100 | 80 | 55 | 65 | 100 | 60 | 100 | 95 | 75 | 0 | 100 | 70 | 100 |
| 11 | 60 | 85 | 70 | 40 | 40 | 98 | 35 | 98 | 45 | 70 | 0 | 100 | 20 | 100 |
| 12 | 50 | 100 | 50 | 25 | 0 | 80 | 10 | 80 | 10 | 80 | 0 | 95 | 0 | 20 |
| 13 | 0 | 0 | 0 | 0 | 0 | 20 | 0 | 20 | 0 | 0 | 0 | 60 | 0 | 10 |
| 20 | 35 | 80 | 30 | 30 | 10 | 40 | 30 | 80 | | 40 | 30 | 50 | 20 | 90 |

TEST 6

Aquatic Herbicide Test

The aquatic weeds against which representative compounds were evaluated in this test were coontail, *Ceratophyllum demersum*, L.; *Hydrilla verticillata* (L. F.); and duckweed, *Lemna minor* L. The weeds were prepared by cutting 10-cm. terminal sprigs of coontail and hydrilla, and collecting approximately enough duckweed to cover the surface of the water in a 10-ml. beaker. The weeds were then placed in plastic cartons containing 785 ml. of dechlorinated water containing the compound.

The compounds for this test were formulated as follows. Twenty mg. of compound was weighed into a vial. To the compound was added 1 ml. of acetone, followed by 9 ml. of aqueous 0.1% polyoxyethylenesorbitanmonooleate solution. A 4 ml. aliquot of the aqueous solution or dispersion of the compound was then pipetted into a plastic carton to obtain a concentration of 10 parts per million by weight (ppm.) of the test compound. The cartons were covered with plastic lids and placed on tables at about 24°–25°, in a room where the illumination was about 70–100 foot candles.

Observations of the efficacy of the compound were made 7 days after treatment. The effects were rated on the 1–5 scale. It must be pointed out, however, that the observation period is hardly long enough for the full effect of these compounds to become observable, because of their slow action. Accordingly, a rating of even 2 or 3 in these tests indicates activity.

TEST 7

Algicide Test

Representative compounds were tested against algae species at 10 ppm. concentration. The algae used in this test were *Chlorella vulgaris, Scenedesmus quadricauda, Anacystis nidulans,* and *Stichococcus bacillaris.* Cultures of these algae were grown on artificial media, and were used in this test when they were from 3 to 7 days old. The algae cultures were diluted for use in these tests by adding 5 ml. of Anacystis culture, or 1 ml. of the other cultures, to 500 ml. of sterile growth medium. In some instances, other amounts of inoculated medium were used.

The compounds were formulated as described in Test 6 above, and the correct amount of formulated compound was added to each portion of algae-inoculated medium to provide a concentration of 10 ppm. of the compound.

The treated and untreated control algae cultures were stored as described in Test 1, and were observed after 7 days. Algicidal effects of the compounds were rated on the 1–5 scale.

Table 7 below reports typical aquatic herbicide and algicide tests. In some instances, tests were carried out at rates other than 10 ppm. In these instances, the rate is indicated in the table in parenthesis next to the example number of the compound.

TABLE 7

| Compound of Example No. | Hydrilla | Coontail | Duckweed | Chlorella | Scenedesmus | Anacystis | Stichococcus |
|---|---|---|---|---|---|---|---|
| 1 | 3 | 3 | 3 | 1 | 5 | 5 | |
| 2 | 3 | 3 | 3 | 2 | 5 | 3 | |
| 4 | | | | 1 | 5 | 4 | 1 |
| 5 | | | | | | | |
| 7 | 3 | 3 | 3 | 5 | 5 | 5 | |
| 10 | | | | 5 | 5 | 4 | 1 |
| 10(2) | 4 | 4 | 4 | | | | |
| 10(.5) | | | | 4 | 5 | 5 | 1 |
| 16 | | | | 1 | 3 | 4 | 1 |
| 20 | | | | 1 | 5 | 4 | 1 |
| 21 | 3 | 3 | 3 | 1 | 5 | 4 | |
| 22 | 3 | 3 | 3 | 1 | 5 | 5 | |

The compound of Example 10 was also tested against four other species of algae, *Chlamydomonas moewus,* Anabaena strain B378, Anabaena strain 1551, and Anabaena strain 1552. When the compound of Example 10 was tested against these algae at a concentration of 1 ppm., the results were rated as 3,3,1,1 respectively, and, when the same compound was tested at 0.5 ppm., the results were 2,2,1,1 respectively.

TEST 8

Herbicide Field Test

Representative compounds were tested in cotton cropland in the Midwestern United States. The cotton was grown in a silty loam soil with about 2% organic matter content. The cotton was planted in rows, and each test plot included a 4.5-meter length of 2 rows.

The compounds were formulated, the compound of Example 6 as an emulsifiable concentrate containing 1 lb./gal. of compound, and the compound of Example 10 as an emulsifiable concentrate containing 2 lb./gal. The formulated compounds were emulsified in water for application; the emulsion volume was 282 liters/hectare in all cases. In some tests, the compound was sprayed on the surface of the soil and left there, and in others the compound was incorporated in the soil with a rotary tiller to a depth of 7–10 cm. immediately application.

The cotton was planted immediately after application of the compound to the test plots. It was not irrigated during the experiment, but received adequate rainfall for growth.

Three replicate plots were used for each treatment variation. About 3 and 6 weeks after the test was established, the plots were observed by an experienced observer, who rated the weed control, compared to untreated control plots. The results are recorded in the table below. Results from the replicate plots have been averaged. The abbreviation "SA" is used to indicate surface application of the compounds, and "PPI" indicates incorporated applications. The cotton crop was also observed for injury, which is reported as percent injury, compared to the untreated control plots.

TABLE 8

| Compound of Example No. | Application Rate kg./ha. | Percent Control | | | | | |
|---|---|---|---|---|---|---|---|
| | | Crop Injury | | Setaria italica | Annual grasses | Ipomoea Spp. | |
| | | 3 wk. | 6 wk. | 3 wk. | 6 wk. | 3 wk. | 6 wk. |
| 6 | 0.14 PPI | 0% | 0% | 20% | 25% | 0% | 0% |
| 6 | 0.28 PPI | 0 | 0 | 62 | 62 | 67 | 17 |
| 6 | 0.56 PPI | 0 | 0 | 82 | 77 | 93 | 52 |

TABLE 8-continued

| Compound of Example No. | Application Rate kg./ha. | | Crop Injury | | Percent Control Setaria italica | Annual grasses | Ipomoea Spp. | |
|---|---|---|---|---|---|---|---|---|
| | | | 3 wk. | 6 wk. | 3 wk. | 6 wk. | 3 wk. | 6 wk. |
| 6 | 1.1 | PPI | 7 | 0 | 90 | 85 | 100 | 92 |
| 6 | 0.28 | SA | 0 | 0 | 10 | 8 | 0 | 0 |
| 6 | 0.56 | SA | 0 | 0 | 17 | 22 | 0 | 0 |
| 6 | 1.1 | SA | 0 | 0 | 53 | 45 | 37 | 7 |
| 6 | 2.2 | SA | 0 | 0 | 70 | 58 | 70 | 13 |
| 10 | 0.14 | PPI | 0 | 7 | 10 | 18 | 20 | 7 |
| 10 | 0.28 | PPI | 0 | 12 | 62 | 62 | 50 | 17 |
| 10 | 0.56 | PPI | 5 | 2 | 90 | 87 | 97 | 63 |
| 10 | 1.1 | PPI | 0 | 2 | 98 | 92 | 100 | 96 |
| 10 | 0.28 | SA | 0 | 0 | 10 | 13 | 0 | 0 |
| 10 | 0.56 | SA | 0 | 0 | 42 | 30 | 27 | 10 |
| 10 | 1.1 | SA | 7 | 3 | 63 | 50 | 60 | 5 |
| 10 | 2.2 | SA | 0 | 0 | 73 | 62 | 77 | 42 |

Plant scientists will recognize that the compounds of this invention are broadly effective against unwanted herbaceous plants, including terrestrial and aquatic plants and algae, which will together be here referred to as weeds for the sake of brevity. Accordingly, an important embodiment of this invention is the use of the compounds to reduce the vigor of such weeds by contacting the weed with an herbicidally-effective amount of a compound of this invention. In the context of this invention, weed seeds are included in the term "weeds".

It will be observed that the compounds are effective in reducing the vigor of weeds when applied both preemergence and postemergence. Thus, they can be applied to the soil to affect weeds by soil contact when the weeds are germinating and emerging, and can also be used against emerged weeds by direct contact with the exposed portions of the weed. It is preferred but not necessary to incorporate the compounds in the soil when they are applied preemergence. When the compounds are used against aquatic weeds, they can be applied to the water in which the weeds grow, or to the sub-aqueous soil, and similarly they can be applied effectively either before or after germination of the aquatic weeds.

The term "reduce the vigor of" is used here to refer to both killing and injuring the weeds or algae which are contacted with a compound. In many instances, as is clear from the test results, the whole population of the weed is killed. In other instances, part of the weeds are killed and part of them are injured, and in still other instances, none of the weeds are killed but are merely injured by application of the compound. It will be understood that reducing the vigor of the weed or algae population by injuring part of them is beneficial, even though part of the population survives application of the compound. The weeds or algae, the vigor of which has been reduced, are unusually susceptible to the normal stresses which afflict plants, such as disease, drought, lack of nutrients and so forth.

As the tests above illustrate, many of the compounds of this invention are acceptably safe to a number of crops. It will be noted that the compounds are particularly harmless to cotton in the exemplified experiments. Because of the safety with which this crop may be treated with the compounds, the use of the method against weeds in cotton cropland is a preferred embodiment of the invention.

It is not implied, of course, that all compounds of this invention are effective against all weeds and algae at all application rates. Some compounds are most effective against some species, other compounds are more effective against others. All of the compounds, however, are effective against at least some weeds and algae. It is within the ordinary skill of a plant scientist to acertain the weeds which are most advantageously controlled with the various compounds, and the optimum application rate for a given use.

In general, application rates against terrestrial weeds range from about 0.1 kg./ha. to about 20 kg./ha. The optimum rates will usually be found to be within the preferred range of from about 0.5 kg./ha. to about 10 kg./ha. The same rates are used, in general, against aquatic weeds and algae. It will be understood that many factors affect the choice of application rate against a given species, including the method of compound application, weather, soil type, organic matter content of the soil (including the sub-aqueous soil, in the case of aquatic applications) and the hardness and suspended organic matter content of the water.

In some instances, aquatic applications of the compounds should be measured by the concentration of the compound in the water. In particular, it is best to measure the application rate by concentration when the body of water is quite deep, or when the water is flowing or is often disturbed by wind or thermal effects. Under such circumstances, concentrations from about 0.1 ppm. to about 15 ppm. are effective. More preferably, rates from about 1 ppm. to about 10 ppm. are used.

The time when the compounds should be applied to the soil, weeds or water is widely variable, since the compounds are effective both preemergence and postemergence. At least some control of weeds will result from application of the compounds at any time when weeds are growing or germinating. They may also be applied to the soil during a dormant season to control weeds germinating during the following warm season.

When the compounds are used for weed control in an annual crop, it is usually best to apply a preemergence application of the compound to the soil at the time the crop is being planted. If the compound is to be soil incorporated, it will usually be applied and incorporated immediately before planting. If it is to be surface applied, it is usually simplest to apply the compound immediately after planting.

The compounds are applied to the soil, emerged weeds or water in the manners usual in agriculture. They may be applied in the form of either water-dispersed or granular formulations, the preparation of which will be discussed below. Usually, water-dispersed formulations will be used for the application of the compounds to emerged weeds. The formulations are applied with any of the many types of sprayers and granular applicators which are in wide use for the distribution of agricultural chemicals. When a compound is to be soil-incorporated, any of the usual soil incorporation equipment, such as the disc harrow, the power-driven rotary hoe and the like, are effective.

The compounds are normally used in the practice of the method of this invention in the form of the herbicidal compositions which are an important embodiment of the invention. A herbicidal composition of this invention comprises a compound of the invention and an inert carrier. In general, the compositions are formulated in the manners usual in agricultural chemistry, and are novel only because of the vital presence of the novel herbicidal compound.

Herbicidal compositions of this invention contain from about 0.5% to about 90% by weight of a compound of this invention, and are of various types. The most important types of compositions are concentrated formulations which are dispersed in water for application. The compositions also include, however, dry granular compositions which are applied as such to the soil or the water in which weeds are to be controlled. Those skilled in agricultural chemistry are aware of the manners in which agricultural compositions are formulated, but some discussion of the compositions will be given to assure that the reader fully understands the invention.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form wettable granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and non-ionic surfactants such as ethylene oxide adducts of alkyl phenol.

Emulsifiable concentrates of the compounds comprise a convenient concentration of the compound, such as from about 10% to about 50% by weight of liquid, dissolved in an inert carrier which is a mixture of water-immiscible organic solvent and emulsifiers. Useful organic solvents include the aromatics, especially the xylenes, and the petroleum fractions, especially the high-boiling napthalenic and olefinic portions of petroleum such as heavy aromatic naphtha. Other organic solvents may also be used, such as the terpenic solvents including rosin derivatives, and complex alcohols such as 2-ethoxyethanol. Suitable emulsifiers for emulsifiable concentrates are chosen from the same types of surfactants discussed above.

Aqueous suspensions comprise suspensions of water-insoluble compounds of this invention, usually the feee base forms, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts, may also be added, to increase the density of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for preemergence applications to the soil and for applications to water, where it is desired to apply the compound to the sub-aqueous soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been preformed to the appropriate particle size, in the range of from about 0.5 to about 3 ml. Such compositions may also be formulated by making a dough or paste of the carrier and compound, and crushing and drying to obtain the desired granular particle size.

The following formulae are exemplary of typical formulations of the compounds, which are referred to here by their example numbers. The formulae are in percent by weight.

| Wettable Powders | |
|---|---|
| I. | |
| Example 2 | 10% |
| sodium lauryl sulfate | 6 |
| sulfonated lignin | 3 |
| attapulgite clay | 81 |
| II. | |
| Example 6 | 50% |
| alkyl sulfonate | 5 |
| polyoxyethylene ether | 1 |
| colloidal silica | 3 |
| kaolin clay | 41 |
| III. | |
| Example 7 | 90% |
| alkyl sulfate | 1 |
| sodium lignin sulfonate | 0.5 |
| colloidal silica | 8.5 |
| IV. | |
| Example 10 | 75% |
| calcium alkyl sulfonate | 3 |
| naphthalene sulfonate | 2 |
| colloidal silica | 1 |
| montmorillonite clay | 19 |

| Emulsifiable Concentrates | |
|---|---|
| I. | |
| Example 10 | 25% |
| 2-methoxyethanol | 20 |
| sulfonate/polyoxyethylene ether blend | 5 |
| xylene | 50 |
| II. | |
| Example 6 | 12.5% |
| sulfonate/polyoxyethylene ether blend | 5 |
| 2-methoxyethanol | 20 |
| xylene | 62.5 |
| III. | |
| Example 12 | 50% |
| metal sulfonate/polyoxyether blend | 10 |
| 2-ethoxyethanol | 30 |

| -continued | |
|---|---|
| xylene | 10 |
| Granules | |
| I. | |
| Example 1 | 0.5% |
| Attapulgite | 99.5 |
| II. | |
| Example 22 | 4% |
| Bentonite | 96 |
| III. | |
| Example 19 | 10% |
| Kaloin | 90 |

I claim:

1. A compound of the formula

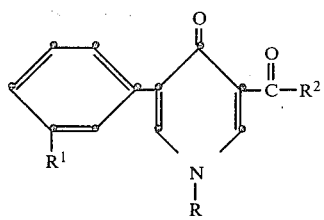

wherein R is $C_1-C_3$ alkyl; $R^1$ is chloro, bromo, fluoro or trifluoromethyl; $R^2$ is $C_1-C_4$ alkyl, phenyl, $C_1-C_2$ alkyl substituted with chloro or bromo or monosubstituted with methoxy, or phenyl monosubstituted with chloro, bromo, fluoro or trifluoromethyl.

2. A compound of claim 1 wherein R is methyl.

3. A compound of claim 2 wherein $R^1$ is trifluoromethyl.

4. A compound of claim 3 wherein $R^2$ is $C_1-C_4$ alkyl.

5. A compound of claim 3 wherein $R^2$ is $C_1-C_2$ alkyl substituted with chloro.

6. The compound of claim 1 which is 1-methyl-3-propionyl-5-(3-trifluoromethylphenyl)-4(1H)-pyridinone.

7. The compound of claim 1 which is 3-acetyl-1-methyl-5-(3-trifluoromethylphenyl)-4(1H)-pyridinone.

8. The compound of claim 1 which is 3-butyryl-1-methyl-5-(3-trifluoromethylphenyl)-4(1H)-pyridinone.

9. The compound of claim 1 which is 1-methyl-3-(2,2-dimethylpropionyl)-5-(3-trifluoromethylphenyl)-4(1H)-pyridinone.

10. The compound of claim 1 which is 1-methyl-3-(2-methylpropionyl)-5-(3-trifluoromethylphenyl)-4(1H)-pyridinone.

11. A method of reducing the vigor of weeds which comprises contacting the weed with an herbicidally-effective amount of a compound of claim 1.

12. A method of claim 11 wherein the amount of the compound is from about 0.1 kg./ha. to about 20 kg./ha.

13. A method of claim 12 wherein the amount of the compound is from about 0.5 kg./ha. to about 10 kg./ha.

14. A method of claim 13 wherein the weeds are in the soil of cotton cropland.

15. A method of claim 14 wherein the compound is incorporated in the soil.

16. A method of claim 11, 13 or 15 wherein the compound is a compound wherein R is methyl and $R^1$ is trifluoromethyl.

17. A method of claim 11, 13 or 15 wherein the compound is 1-methyl-3-propionyl-5-(3-trifluoromethylphenyl)-4(1H)-pyridinone.

18. A method of claim 11, 13 or 15 wherein the compound is 3-acetyl-1-methyl-5-(3-trifluoromethylphenyl)-4(1H)-pyridinone.

19. A method of claim 11, 13 or 15 wherein the compound is 3-butyryl-1-methyl-5-(3-trifluoromethylphenyl)-4(1H)-pyridinone.

20. A method of claim 11, 13 or 15 wherein the compound is 1-methyl-3-(2,2-dimethylpropionyl)-5-(3-trifluoromethylphenyl)-4(1H)-pyridinone.

21. A method of claim 11, 13 or 15 wherein the compound is 1-methyl-3-(2-methylpropionyl)-5-(3-trifluoromethylphenyl)-4(1H)-pyridinone.

22. An herbicidal composition comprising an inert carrier and a compound of claim 1.

23. A composition of claim 22 wherein the compound is a compound wherein R is methyl and $R^1$ is trifluoromethyl.

24. A composition of claim 22 wherein the compound is 1-methyl-3-propionyl-5-(3-trifluoromethylphenyl)-4(1H)-pyridinone.

25. A composition of claim 22 wherein the compound is 3-acetyl-1-methyl-5-(3-trifluoromethylphenyl)-4(1H)-pyridinone.

26. A composition of claim 22 wherein the compound is 3-butyryl-1-methyl-5-(3-trifluoromethylphenyl)-4(1H)-pyridinone.

27. A composition of claim 22 wherein the compound is 1-methyl-3-(2,2-dimethylpropionyl)-5-(3-trifluoromethylphenyl)-4(1H)-pyridinone.

28. A composition of claim 22 wherein the compound is 1-methyl-3-(2-methylpropionyl)-5-(3-trifluoromethylphenyl)-4(1H)-pyridinone.

* * * * *

UNITED STATES PATENT AND TRADEMARK OFFICE
CERTIFICATE OF CORRECTION

PATENT NO. : 4,319,916
DATED : March 16, 1982
INVENTOR(S) : Riaz F. Abdulla

It is certified that error appears in the above—identified patent and that said Letters Patent is hereby corrected as shown below:

Column 5, Lines 63-66, the formula which reads
$$\text{"}\begin{array}{c} Q^3-R^4 \\ | \\ HHCN(R^3)_2 \\ | \\ Q^3-R^4 \end{array}\text{"}$$

should read --
$$\begin{array}{c} Q^3-R^4 \\ | \\ HCN(R^3)_2 \\ | \\ Q^3-R^4 \end{array}$$
--.

𝕾igned and 𝕾ealed this

First Day of June 1982

[SEAL]

Attest:

Attesting Officer

GERALD J. MOSSINGHOFF

Commissioner of Patents and Trademarks